US007923672B2

(12) United States Patent
Wolleschensky

(10) Patent No.: US 7,923,672 B2
(45) Date of Patent: Apr. 12, 2011

(54) PROCESS AND DEVICES FOR OPTICALLY SENSING A SPECIMEN WITH A LARGE DEPTH OF FIELD

(75) Inventor: Ralf Wolleschensky, Jena (DE)

(73) Assignee: Carl Zeiss Microimaging GmbH, Jena (DE)

( * ) Notice: Subject to any disclaimer, the term of this patent is extended or adjusted under 35 U.S.C. 154(b) by 253 days.

(21) Appl. No.: 12/088,610

(22) PCT Filed: Sep. 14, 2006

(86) PCT No.: PCT/EP2006/008945
§ 371 (c)(1), (2), (4) Date: Mar. 28, 2008

(87) PCT Pub. No.: WO2007/036304
PCT Pub. Date: Apr. 5, 2007

(65) Prior Publication Data
US 2009/0159800 A1 Jun. 25, 2009

(30) Foreign Application Priority Data
Sep. 29, 2005 (DE) .......................... 10 2005 046 754

(51) Int. Cl.
*G01B 7/04* (2006.01)
*G01B 9/02* (2006.01)
*G01D 5/36* (2006.01)

(52) U.S. Cl. .................. 250/201.3; 356/485; 250/237 G

(58) Field of Classification Search .................. 250/362, 250/237 G, 201.3, 201.9, 282; 356/4.09, 356/485, 409; 382/154, 141; 348/136
See application file for complete search history.

(56) References Cited

U.S. PATENT DOCUMENTS
2002/0018118 A1    2/2002    Coulombe
(Continued)

FOREIGN PATENT DOCUMENTS
DE    102 57 237 A1    6/2003
(Continued)

OTHER PUBLICATIONS

Nil, M.A.A., et al.; "Method ofr obtaining optical sectioning by using structured light in a conventional microscope", Optics Letters 1997; 22(24):1905-1907.

*Primary Examiner* — David P Porta
*Assistant Examiner* — Faye Boosalis
(74) *Attorney, Agent, or Firm* — Duane Morris LLP

(57) ABSTRACT

A device for optically sensing a specimen with a large depth of field has a lighting module which illuminates a zone of the specimen during a predetermined measurement period with a pattern whose phase is modified in time during the measurement period, generating a specimen light to which a corresponding time-variable phase is imparted. The device also includes a detection module having a space-resolving detection zone which records the specimen zone and has multiple recording pixels, two analysis channels which can be connected to the recording pixels, and an analysis unit is connected to both analysis channels. A control unit is provided which, during the measurement period, connects each recording pixel in synchrony with the phase of the detected specimen light to the two analysis channels, alternatively, in such a way that the detected specimen light is divided into two portions phased in relation to one another, and the analysis unit calculates an optical split-image of the specimen zone on the basis of the two phased portions supplied to the analysis channels.

14 Claims, 3 Drawing Sheets

U.S. PATENT DOCUMENTS

2005/0046865 A1 * 3/2005 Brock et al. .................. 356/495

FOREIGN PATENT DOCUMENTS

| | | |
|---|---|---|
| DE | 102 54 139 A1 | 5/2004 |
| DE | 10 2005 046 754.7 | 9/2005 |
| EP | 00 76 866 A1 | 4/1983 |
| WO | WO 97/06509 A1 | 2/1997 |
| WO | WO 98/45745 A | 10/1998 |
| WO | WO 01/71279 A | 9/2001 |

* cited by examiner

PROCESS AND DEVICES FOR OPTICALLY SENSING A SPECIMEN WITH A LARGE DEPTH OF FIELD

RELATED APPLICATIONS

The present application is a U.S. National Stage application of International PCT Application Number PCT/EP2006/008945 filed on Sep. 14, 2006, which claims the benefit of German Application Number DE 10 2005 046 754.7 filed on Sep. 29, 2005, the contents of each of which are incorporated by reference in their entirety.

FIELD OF THE INVENTION

The invention relates to a device and a method for optically sensing a specimen. In particular, it relates to the field of so-called structured illumination, in which the modulation depth of the optical imaging of an amplitude structure (such as a grating) is used as the criteria for the depth of field. The image of the periodic structure is distinguished by the frequency of the modulation and the phase position (image phase) of the modulation. Different projection scenarios can be obtained by a phase shift of the structure perpendicular to the optical axis. For instance, three phase images at 0°, 120° and 240° are required to be able to calculate a depth-discriminated optical section, as is described, for example in M. A. A. Nil et al., "Method of obtaining optical sectioning by using structured light in a conventional microscope," Optics Letters 22 (24) 1997, pp. 1905-1907. The disadvantage in this case is that several images must be successively recorded, read out and calculated.

BACKGROUND OF THE INVENTION

In order to be able to generate images at a detector to the extent possible, so that a limitation of the dynamic range by non-confocal background signals is prevented, it is proposed in DE 10254139 A1 that components of the detection or specimen light having a phase shift with respect to one another be spatially subdivided. This has the disadvantage, however, that in case of a linear illumination, for instance, at least two detector rows must be provided.

SUMMARY OF THE INVENTION

Starting from this basis, the object of the invention is to provide a method or a device for optical sensing of a specimen with a large depth of field in which the disadvantages mentioned above can be avoided.

According to the invention, the problem is solved by a device for optical sensing of a specimen with a large depth of field, with an illumination module that illuminates an area of the specimen during a predetermined measurement period with a pattern, the phase of which is varied over time, whereby specimen light to which a corresponding time-varying phase has been imparted is generated. The invention also includes: a detection module having a space-resolving detection area with several recording pixels, two analysis channels connectable to the recording pixels, as well as an analysis unit connected to the two analysis channels; and a control unit that connects, during the measurement period, each recording pixel alternately to the two analysis channels synchronously with the phase of the detected specimen light, so that the detected specimen light is subdivided into two components having a phase shift with respect to one another, and is supplied to the two analysis channels, wherein the analysis unit calculates an optical section image based on the components supplied to the two analysis channels.

Due to the provision of two separate analysis channels and the possibility of connecting the recording pixels alternately to the one or the other analysis channel, the two phase components of the specimen light can be sensed with the same recording pixels, so that the dynamic range of the detector is not limited by non-confocal background light.

The specimen light can be produced from an interaction of the light from the illumination module with the specimen, in particular, the specimen light can be fluorescent light, reflected light, luminescence light, scattered light and/or transmitted light.

The pattern with which the specimen is illuminated is a predetermined intensity distribution of the illumination light; in particular, a periodic pattern or a periodic intensity distribution such as a sinusoidal distribution is generated. The time-variation of the phases is also preferably performed in a periodic manner. Here as well, a sinusoidal or cosinusoidal phase change can be performed.

The control unit can connect the recording pixels alternately to the two analysis channels in such a manner that the phase shift is 180° ($\pi$). An optimal result in the calculation of the sectional image is obtained in this manner.

Each recording pixel can have two subpixels, of which one of the subpixels is connectable only to one of the two analysis channels, and the other only to the second analysis channel. In this manner, the detection module can be easily realized.

The recording pixels can be arranged side by side along one extension direction. In particular, a linear detection area can be realized in this way. This is of particular advantage if the illumination module illuminates the specimen linearly and the linear illumination is deflected over the specimen transversely to the direction of extension, since the linearly illuminated specimen area is always recorded in this case by means of the detection area. This can be implemented particularly easily with the device constructed as a laser scanning microscope, since the scanner for the deflection of the illumination light is generally also used to de-scan the specimen light.

More particularly, each of the analysis channels can be constructed as a separate analysis electronic unit. A fast and exact phase-dependent sensing of the components of the specimen light thereby becomes possible.

For each recording pixel, each analysis channel can have an integrator that sums the supplied components during the measurement period.

The analysis unit for calculating the optical sectional image can additionally subtract the two (preferably summed-up) components from one another. Thus the detection module can carry out all essential (particularly time-intensive) analyses in hardware, so that the image data basically needs only to be displayed to generate the sectional image. It is of course possible to record several optical sections in different parts of the specimen and to create a corresponding three-dimensional representation from them by known methods.

In case of a linear detection, the phase variation is preferably performed in the direction of linear detection.

The invented device for optical sensing of a specimen with large depth of field is constructed in particular is a microscope. The microscope can be a laser scanning microscope.

According to the invention, a method for optical sensing of a specimen with large depth of field is additionally provided, in which an area of the specimen is illuminated during a predetermined measuring period with a pattern whose phase is varied temporally during the measurement, whereby specimen light is generated, to which a corresponding time-varying phase has been imparted, and in which the specimen area is detected in a space-resolving matter during the measurement period, and the detected specimen light is subdivided into two components having a phase shift with respect to one another, wherein an optical sectional image of the specimen area is calculated on the basis of the components. With this method, an optical sectional image can be obtained quickly and with high accuracy.

It is particularly preferred if the detected specimen light is subdivided with a phase shift of 180°. Then very good results can be obtained.

Several recording pixels can be provided in this method for space-resolving detection, each recording pixel having two subpixels and one of the subpixels supplying the first of the two components and the other of the two subpixels, the second component.

Moreover a linear, space-resolving detection can be performed. In this case space-resolving line detectors can be used.

In this method a separate analysis electronic unit, comprising an integrator for instance, which sums the supplied components in a space-resolving manner over the measurement period, can additionally be provided for each component. Thus, the essential (in particular, the time-intensive) analysis for generating the optical section with a large depth of field can be performed in hardware. Such hardware solutions can usually be operated with very high precision and more rapidly than corresponding solutions implemented in software.

In particular, the two components can be subtracted from one another to calculate the optical sectional image. One can thereby obtain the desired conformal image information.

Additionally, the specimen can be linearly illuminated and the phase can be varied in the direction of the linear illumination. If the linear illumination is scanned across the specimen, the entire specimen can be sensed with only one linear position-resolved detection being necessary.

The invented method for depth-resolved optical sensing of the specimen is, in particular, a microscopy method. The microscopy method can be a laser scanning microscopy method.

BRIEF DESCRIPTION OF THE DRAWINGS

Embodiments of the invention will be explained in detail below with reference to the drawings, in which.

DESCRIPTION OF EMBODIMENTS OF THE INVENTION

Figure 1:
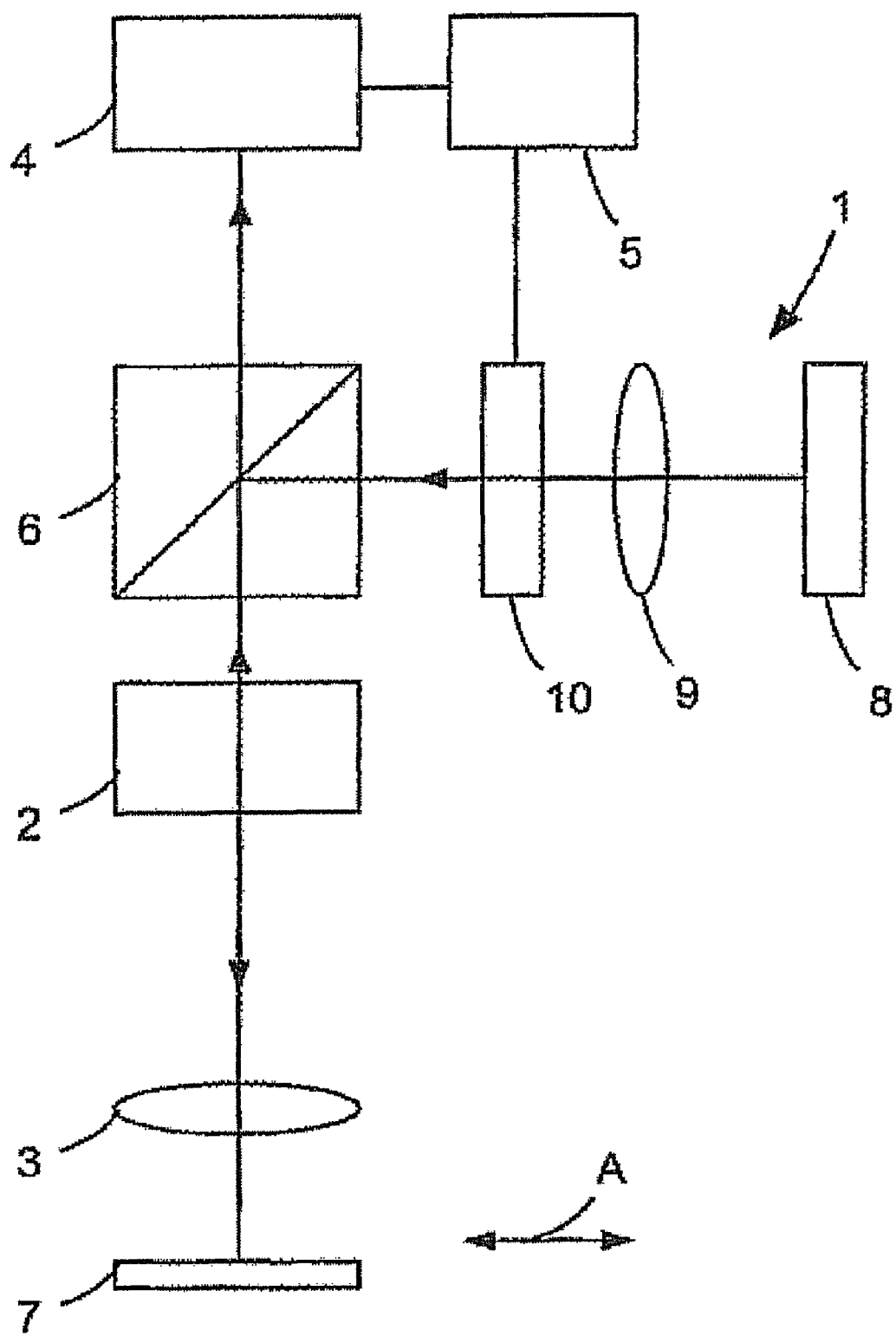
FIG. 1 is a schematic view of one embodiment of the invented device for optical sensing of the specimen with a large depth of field.

In the embodiment shown in FIG. 1, the device for optical sensing of a specimen with a large depth of field is constructed as a laser scanning microscope, which comprises an illumination module 1, a scanning module 2, a microscope module 3, a detection module 4 and a control unit 5.

Illumination module 1 generates a laser beam that is directed to scanning module 2, which deflects the laser beam across specimen 7, via a beam splitter 6 inserted between illumination module 1 and scanning module 2. Illumination module 1 is constructed here such that the laser beam is linearly focused on, or preferably in, specimen 7, with the line extending perpendicular to the plane of the drawing. Scanning module 2 produces a deflection of this linear focus in a direction A perpendicular to the extension direction of the linear focus, so that the entire specimen is illuminated.

Illumination module 1 comprises a laser source 8 for generating a laser beam, optics 9 downstream of laser source 8 to produce the linear focusing, as well as a transmissive amplitude grating 10 which imparts an intensity distribution to the laser beam along the extension direction of the linear focus. This intensity distribution is preferably a periodic intensity distribution, e.g., a cosinusoidal distribution. During operation of the device, amplitude grating 10 is additionally moved rapidly back and forth in the extension direction of the linear focus (i.e., perpendicular to the plane of the drawing in this case), so that a time-varying phase is additionally imparted to the intensity distribution. The back-and-forth motion of amplitude grating 10 is selected such that it is markedly faster than the deflection by means of scanning module 2 so that each linearly illuminated section of specimen 7 is illuminated with a pattern (intensity distribution of amplitude grating 10) whose phase varies over time. For instance, the back-and-forth movement can be sufficiently fast that each linearly illuminated section is illuminated during more than 20, more than 100, or more than 1000 periods of the back-and-forth motion.

In its focus, the focused laser beam brings about the generation of specimen radiation which reaches scanning module 2 via microscope module 3, so that the specimen radiation is present downstream of the scanning module (i.e., between scanning module 2 and beam splitter 6), as a stationary beam. It is therefore often said that scanning module 2 de-scans the specimen radiation. Beam splitter 6 is constructed to transmit the specimen radiation in such a manner that the latter strikes detection module 4.

Figure 2:
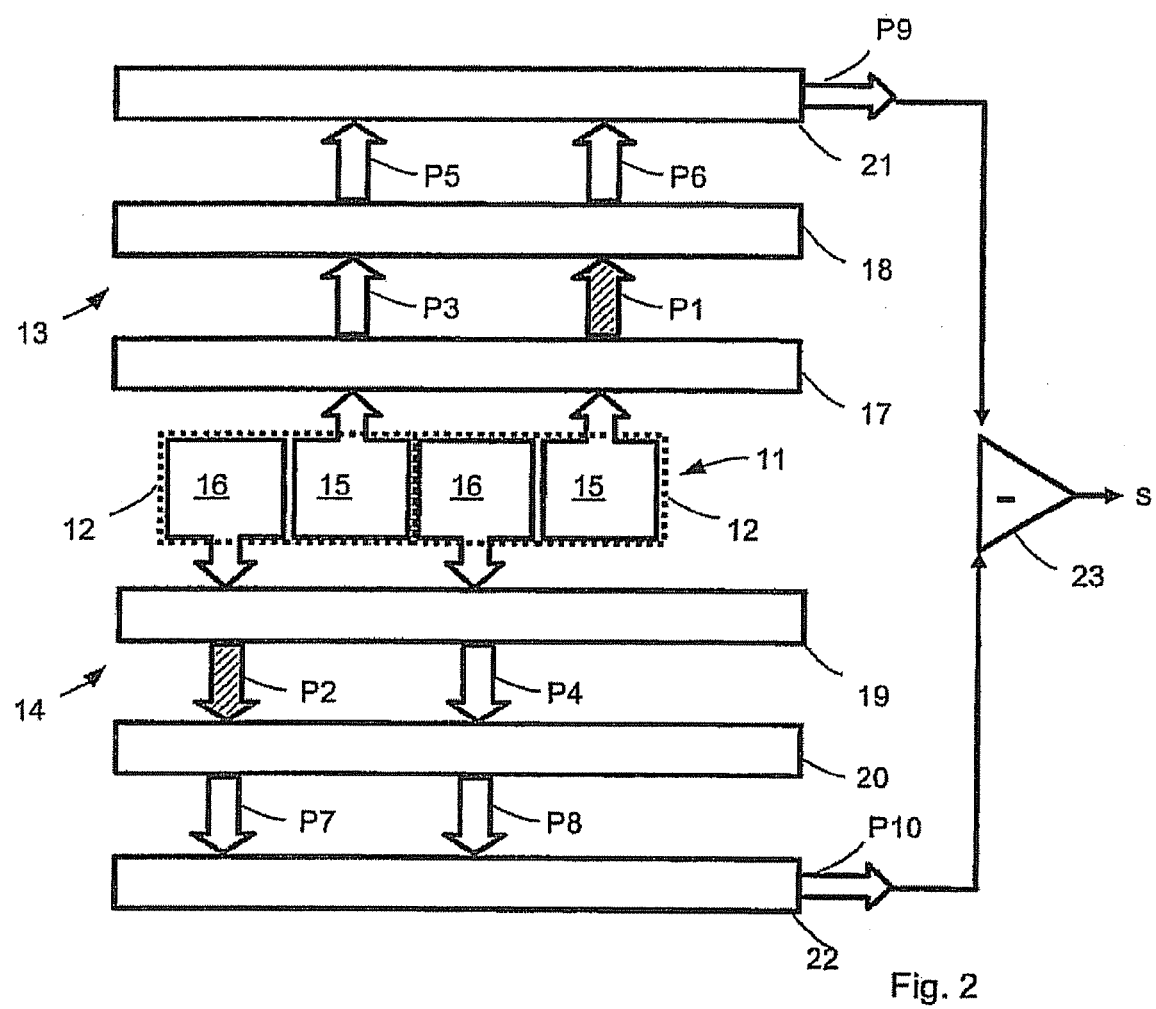
FIG. 2 is an enlarged schematic representation of detection module 4 from FIG. 1.

Detection module 4 comprises, as shown in FIG. 2, a space-resolving, linear detection area 11 with several recording pixels 12. To simplify the illustration only two recording pixels 12 are shown. Of course, the number of recording pixels can be much larger, e.g., 512 or 1024 recording pixels.

Despite the naturally occurring three-dimensional illumination of the specimen, only the plane (optical section) that lies in the focal plane of microscope module 3 can be reproduced by the phase-dependent analysis of the specimen light described below. If one records several sections in different depths of the specimen, a three-dimensional image of the specimen can subsequently be calculated with known methods.

For phase-dependent analysis of the specimen light, analysis channels 13 and 14 are on either of the linearly arranged recording pixels 12, analysis channel 13 sensing the in-phase component of the specimen light, and analysis channel 14 sensing the out-of-phase component of the specimen light. Due to the back-and-forth motion of phase grating 10, the individual points inside the illuminated line in the specimen are sometimes illuminated with maximum intensity and sometimes with minimum intensity. The specimen light that comes from the points illuminated with maximum intensity corresponds to the in-phase component, while the specimen light coming from those points which are illuminated with minimum intensity corresponds to the out-of-phase component.

The association of minimum or maximum intensity with out-of-phase and in-phase components applies in the strict sense only if the intensity distribution of the pattern is rectangular. In the case of a cosinusoidal distribution, for instance, one can determine a threshold value, with specimen light originating from points that are illuminated with an intensity greater than the threshold value corresponding to the in-phase component. On the other hand, specimen light originating from points that are illuminated with an intensity that is not greater than the threshold value corresponds to the out-of-phase component.

One can also say that the in-phase component here corresponds to the signal from the confocal section plus a background signal multiplied by the in-phase component of detection area 11. The in-phase component of detection area 11 corresponds to the grating fowled by the recording pixels 12 that are connected to first channel 13. In the same manner, the out-of-phase component carries the signal from outside the confocal section image plus the background signal multiplied by the out-of-phase component of detection area 11. The out-of-phase component of detection area 11 corresponds to the grating formed by the recording pixels 12 that are connected to second analysis channel 14.

Figure 3:
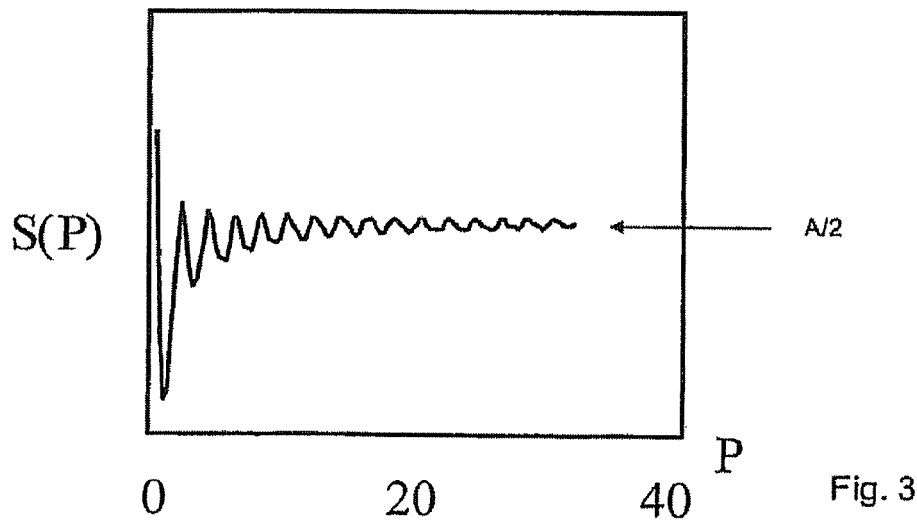
FIG. 3 is a diagram representing the measurement signal as a function of the number of phase-variation periods of the illumination pattern.

The two analysis channels 13 and 14, respectively, integrate or sum the in-phase component and the out-of-phase component for each recording pixel 12 over the dwell time of the linear focus at one point of the specimen. The integrated individual signals for each recording pixel 12 are subsequently subtracted from one another and yield the integrated measurement signal S. For a sufficiently large number of back-and-forth movements, it can be deduced for a cosinusoidal intensity distribution of the linear focus, for instance, that the measurement signal S(P) corresponds to half the signal from the optical sectional image. This signal no longer contains the undesired background signals from planes that lie outside the focus. A corresponding derivation of this relationship can be derived from DE 10254139 A1, wherein the in-phase and out-of-phase components from detection area 11 correspond to the in-phase and out-of-phase components of the structure ST. FIG. 3 schematically shows how measurement signal S approximates the half-signal value A/2 as a function of the number of periods P of back-and-forth movement.

In the detection area 11 shown in FIG. 2, each recording pixel 12 is constructed of two subpixels 15, 16 arranged side by side. Depending on whether the in-phase component or the out-of-phase component strikes pixel 12, either subpixel 15 is connected via a transfer gate 17 to an integrator 18 of the first analysis channel 13, or subpixel 16 is connected via a transfer gate 19 to an integrator 20 of second analysis channel 14.

At a first point in time, subpixel 15 of the right recording pixel 12 in FIG. 2 is thus connected to first analysis channel 13 and subpixel 16 of the left recording pixel 12 is connected to second analysis channel 14 (hatched arrows P1, P2). At a second point in time, however, subpixel 16 of the right recording pixel 12 is connected to second analysis channel 14 and subpixel 15 of the left recording pixel 12 is connected to first analysis channel 13 (arrows P3, P4).

Thus, a splitting of the in-phase component and the out-of-phase components of the specimen line is brought about by selective connection of analysis pixel 12 to first or second analysis channel 13, 14. After all periods of the backward and forward motion of amplitude grating 10 have been completed, the in-phase and out-of-phase measurement signals of integrators 18, 20 generated for recording pixel 12 are supplied via a corresponding shift registers 21, 22 to a subtractor 23 (arrows P5, P6, P7, P8, P9, P10), which subtracts the out-of-phase component from the in-phase component for each recording pixel and thus generates the desired measurement signals S. The desired sectional image can then be generated or calculated from measurement signals S.

Subpixels 15 and 16 of the individual recording pixels 12 naturally need not be arranged side by side as shown in FIG. 2. They can also be arranged one above the other.

The measurement process described here (including the scanning illumination) is controlled by means of control unit 5.

Figure 4:
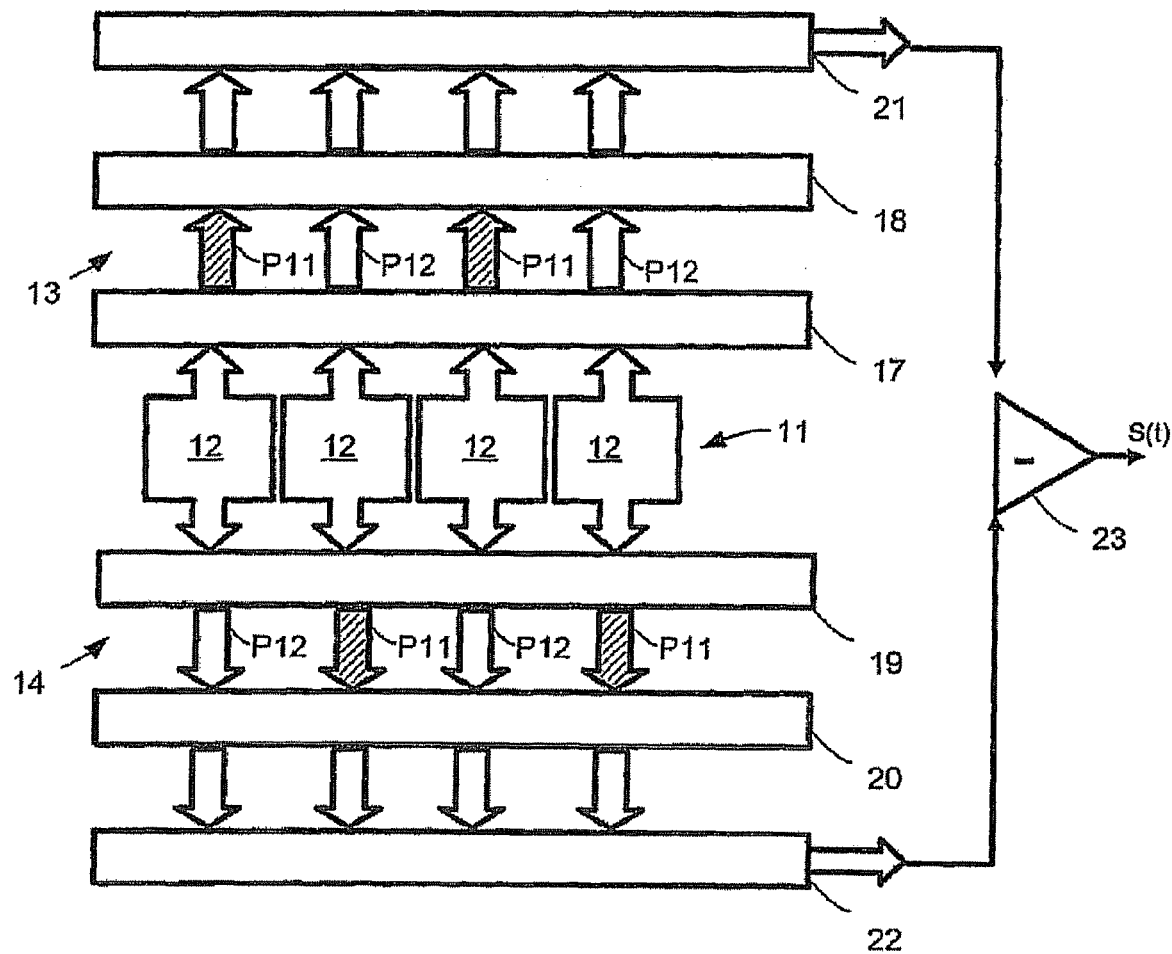
FIG. 4 is an alternative embodiment of detection module 4 from FIG. 1.

A modification of recording module 4 shown in FIG. 2 is represented in FIG. 4. Recording module 4 in FIG. 4 differs from that shown in FIG. 2 in the construction of detection area 11. In detection area 11 of FIG. 4, each recording pixel is constructed from one pixel that can be selectively connected to first or second analysis channel 13, 14. At a first point in time therefore, the first and third analysis pixels 12 (from the left in FIG. 4) can be connected to analysis channel 13 and the second and fourth analysis pixels 12 can be connected to second analysis channel 14 (hatched arrows P11). At a second point in time, the connection of recording pixels 12 to the analysis channels is reversed (arrow P12). After expiration of the measurement period, the summed in-phase and out-of-phase components in integrators 18, 20 are again supplied via shift registers 21, 22 to subtractor 23, which generates the measurement signals S for recording pixels 12. Unlike the construction in FIG. 2, the specimen light is used completely because all recording pixels 12 are always connected either to the first or the second recording analysis channel 13, 14. The resolution is also higher in comparison with the embodiment of FIG. 2, since all pixels always contribute to the image generation.

While the invention has been illustrated and described in connection with currently preferred embodiments shown and described in detail, it is not intended to be limited to the details shown since various modifications and structural changes may be made without departing in any way from the spirit of the present invention. The embodiments were chosen and described in order to best explain the principles of the invention and practical application to thereby enable a person skilled in the art to best utilize the invention and various embodiments with various modification as are suited to the particular use contemplated.

The invention claimed is:

1. A laser scanning microscope, with a laser source to produce a laser beam, in an arrangement where an optical instrument is placed downstream for the linear focusing of the laser beam onto or into a sample, and a scan module to move the laser beam transverse to the extension direction of the line focus above the sample, wherein a periodic intensity distribution is imposed on the laser beam by means of an amplitude grating, arranged in the illumination beam path, in the extension direction of its line focus and the amplitude grating in the microscope is so designed that it is moved back and forth along the extension direction of the line focus to produce a time phase change of the intensity distribution, characterized in that:

a detection module is provided, which has a local resolution detection range, which records the sample area, with several recording pixels, two with evaluation channels that connect the recording pixels, and an evaluation unit connected to the two evaluation channels, and a control unit is provided, which during the measurement time of each recording pixel, synchronous in time with the phase of the detected sample light, alternatingly connects to the two evaluation channels, so that the detected sample light is divided into two fractions, which exhibit a phase shift with respect to one another, and is conducted to the two evaluation channels, wherein each recording pixel has two subpixels, wherein one of the subpixels can be connected only to the first of the two evaluation channels and the other subpixel only to the second evaluation channel.

2. The microscope of claim 1, in which the control unit of each recording pixel connects in such an alternating manner with the two evaluation channels that the phase shift is 180°.

3. The microscope of claim 1, in which the recording pixels are arranged next to one another along one extension direction.

4. The microscope of claim 1, in which each of the evaluation channels is designed as a separate electronic evaluation unit.

5. The microscope of claim 1, in which each evaluation channel has an integrator, which sums up the supplied fractions during the measurement time, for each recording pixel.

6. The microscope of claim 1, in which the evaluation unit subtracts the two fractions from one another for the calculation of the optical cross-section.

7. The microscope of claim 1, wherein an illumination module illuminates the sample linearly and changes the phase in the direction of the linear illumination.

8. A laser scanning microscope method for the deep-resolution optical detection of a sample with a laser beam, focused linearly and moved back and forth over the sample, on which a periodic intensity distribution is imposed, whose phase changes over time during the back and forth movement, whereby a sample area of the sample is illuminated during a predetermined measurement time with a pattern whose phase is changed over time during the measurement time, whereby sample light, on which a corresponding phase changing over time is imposed, is produced and in which the sample area is detected with local resolution during the measurement time, characterized in that:

the detected sample light is divided into two fractions that exhibit a phase shift with respect to one another, and an optical cross-section of the sample area is calculated based on the fractions, wherein by means of a detection module, which has a local-resolution detection area, which records the sample area, with several recording pixels, two evaluation channels, which can be connected to the recording pixels, and an evaluation unit connected to the two evaluation channels, and a control unit, is alternatingly connected to the two evaluation channels during the measurement time of each recording pixel, synchronous in time with the phase of the detected sample light, wherein each recording pixel has two subpixels and one of the subpixels provides only the first of the two fractions and the other subpixel only the second fraction.

9. The method of claim 8, in which the detected sample light is divided with a phase shift of 180°.

10. The method of claim 8, in which a linear, local-resolution detection is carried out.

11. The method of claim 8, in which a separate electronic evaluation unit is provided for each fraction.

12. The method of claim 8, in which an integrator with local resolution and that sums up the supplied fractions over the measurement time is provided.

13. The method of claim 8, in which the two fractions are subtracted from one another for the calculation of the optical cross-section.

14. The method of claim 8, in which the sample is illuminated linearly and the phase is changed in the direction of the linear illumination.

* * * * *